United States Patent [19]

Murphy-Chutorian et al.

[11] Patent Number: 4,832,023
[45] Date of Patent: May 23, 1989

[54] METHOD AND APPARATUS FOR REDUCING BLOCKAGE IN BODY CHANNELS

[75] Inventors: Douglas R. Murphy-Chutorian, Stanford; Walter Y. W. Mok; Kang M. Leung, both of Palo Alto, all of Calif.

[73] Assignee: MCM Laboratories, Inc., Mountain View, Calif.

[21] Appl. No.: 57,791

[22] Filed: Jun. 3, 1987

[51] Int. Cl.$^4$ ............................................. A61B 17/36
[52] U.S. Cl. ............................... 128/303.1; 128/398; 604/96
[58] Field of Search ................. 128/303.1, 395–398; 604/96, 101

[56] References Cited

U.S. PATENT DOCUMENTS

| | | | |
|---|---|---|---|
| 3,471,215 | 10/1969 | Snitzer | 350/96 |
| 3,505,046 | 4/1970 | Phaneuf | 65/3 |
| 3,563,716 | 2/1971 | Li | 65/4 |
| 3,624,816 | 11/1971 | Strack et al. | 350/96 B |
| 3,821,510 | 6/1974 | Muncheryan | 219/121 L |
| 3,858,577 | 1/1975 | Bass et al. | 128/8 |
| 3,865,113 | 1/1976 | Sharon et al. | 128/303.1 |
| 3,933,455 | 1/1976 | Chown | 65/4 |
| 4,072,147 | 2/1978 | Hett | 128/6 |
| 4,080,706 | 3/1978 | Heilman et al. | 128/772 X |
| 4,146,019 | 3/1979 | Bass et al. | 128/6 |
| 4,207,874 | 6/1980 | Choy | 128/6 |
| 4,266,548 | 5/1981 | Davi | 128/303.1 |
| 4,316,467 | 2/1982 | Muckerheide | 128/303.1 |
| 4,398,790 | 8/1983 | Righini et al. | 350/96.18 |
| 4,418,688 | 12/1983 | Loeb | 128/6 |
| 4,445,892 | 5/1984 | Hussein et al. | 128/303.1 X |
| 4,461,283 | 7/1984 | Doi | 128/303.1 X |
| 4,519,390 | 5/1985 | Horne | 128/303.1 |
| 4,556,057 | 12/1985 | Hiruma et al. | 128/303.1 |
| 4,564,011 | 1/1986 | Goldman | 128/303.1 |
| 4,576,177 | 3/1986 | Webster, Jr. | 128/660 |
| 4,627,436 | 12/1986 | Leckrone | 128/303.1 |
| 4,641,650 | 2/1987 | Mok | 128/303.1 |
| 4,641,912 | 2/1987 | Goldenberg | 350/96.10 |
| 4,648,892 | 3/1987 | Kittrell et al. | 65/4.21 |
| 4,662,368 | 5/1987 | Hussein et al. | 128/303.1 |
| 4,669,465 | 6/1987 | Moore et al. | 128/303.1 |
| 4,669,467 | 6/1987 | Willett et al. | 128/303.1 |
| 4,672,961 | 6/1987 | Davies | 128/303.1 |
| 4,681,104 | 7/1987 | Edelman | 128/303.1 |
| 4,682,594 | 7/1987 | Mok | 128/313.1 |
| 4,685,458 | 8/1987 | Leckrone et al. | 128/303.1 |
| 4,723,936 | 2/1988 | Buchbinder et al. | 604/95 |

FOREIGN PATENT DOCUMENTS

| | | |
|---|---|---|
| 0144764 | 6/1985 | European Pat. Off. |
| 0178464 | 4/1986 | European Pat. Off. |
| 3527451 | 2/1986 | Fed. Rep. of Germany ... 128/303.1 |
| WO83/01893 | 6/1983 | World Int. Prop. O. ....... 128/303.1 |
| WO87/01273 | 3/1987 | World Int. Prop. O. ....... 128/303.1 |

Primary Examiner—Lee S. Cohen
Attorney, Agent, or Firm—Irell & Manella

[57] ABSTRACT

An instrument for removing an obstruction in an internal body channel comprises an elongated catheter body adapted for insertion into a body channel having a first lumen throughout its length. An elongated guide and laser transmission conduit extends through the lumen of said catheter body and is movable therein so that its distal end can be extendable beyond the distal end of the catheter body. The proximal end of the movable conduit is connected to a controlled source of laser energy. A treatment element is provided at the distal end of the catheter body for further reducing the channel obstruction following preliminary penetration thereof by the movable laser transmission conduit. The treatment element may be a fixed laser transmission conduit which terminates at the end of the catheter body or a dilation balloon near its distal end. In method steps utilizing the instrument, the movable conduit is positioned near a channel obstruction to enlarge a passage through and then serves to guide the catheter body into position so as to further enlarge or remove the obstruction using its treatment element.

28 Claims, 5 Drawing Sheets

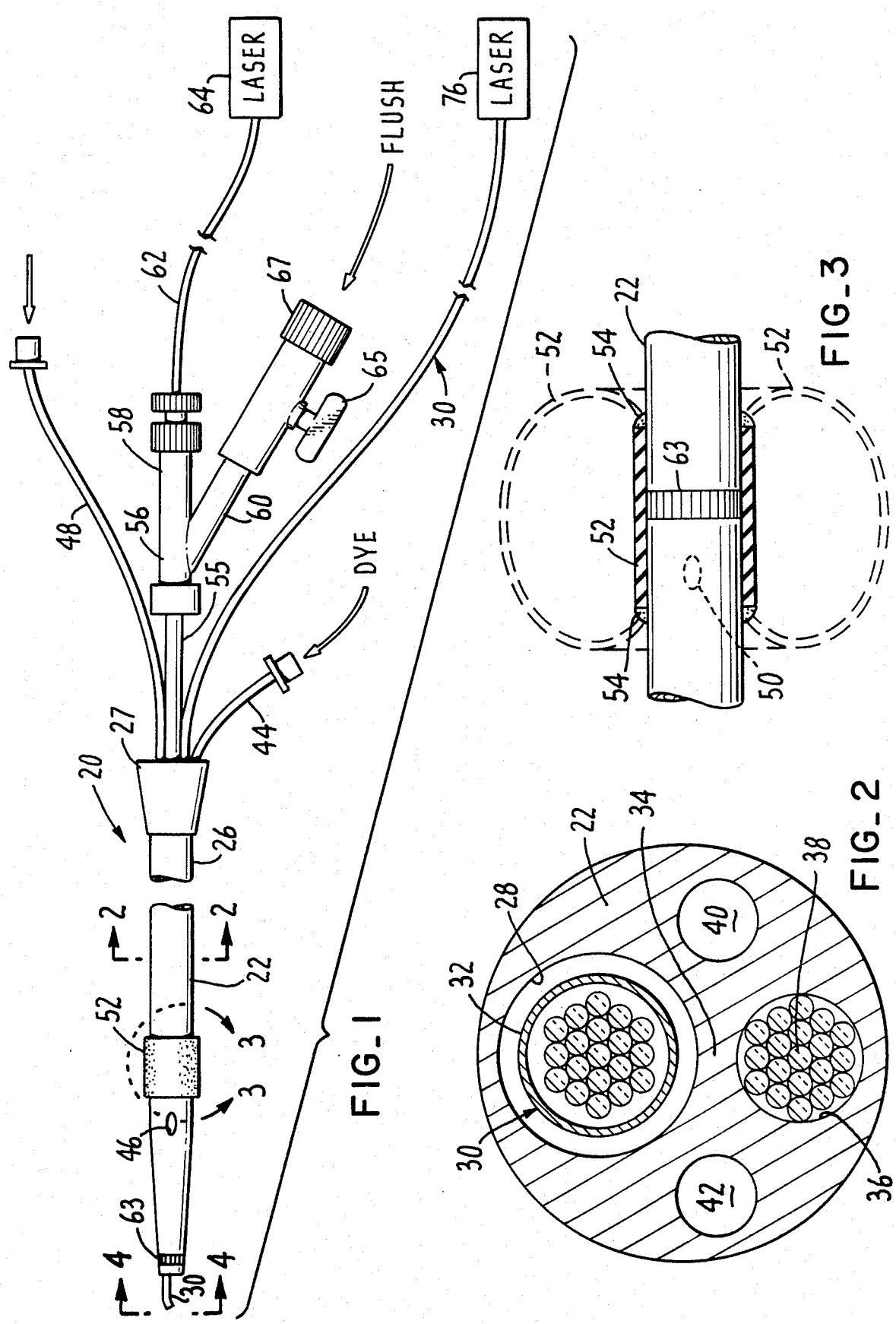

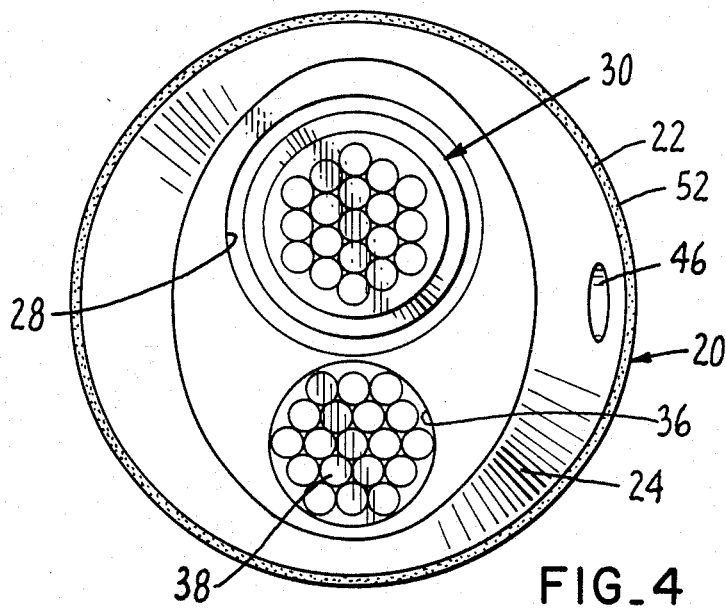
FIG_4
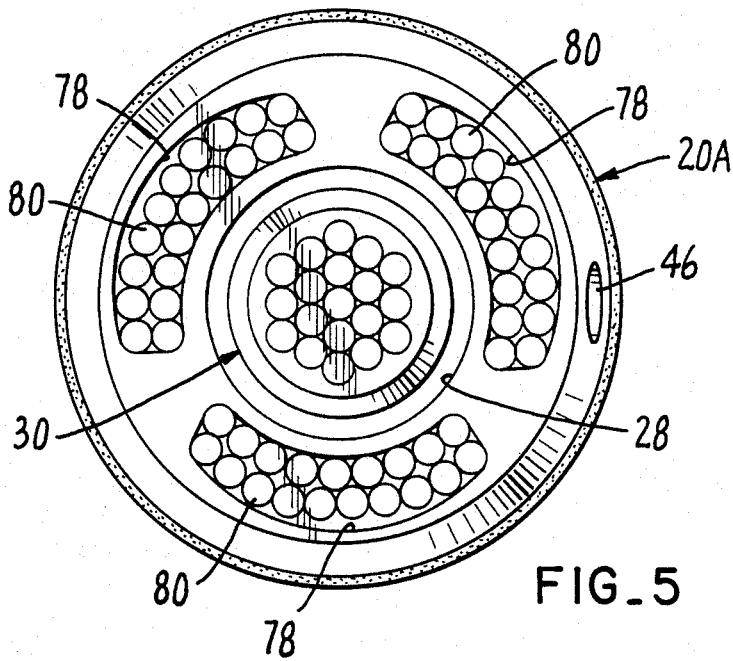
FIG_5

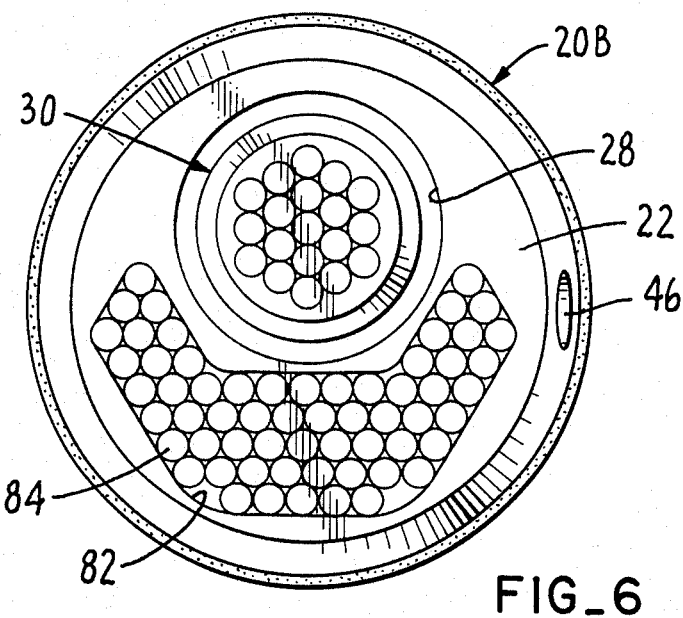
FIG_6
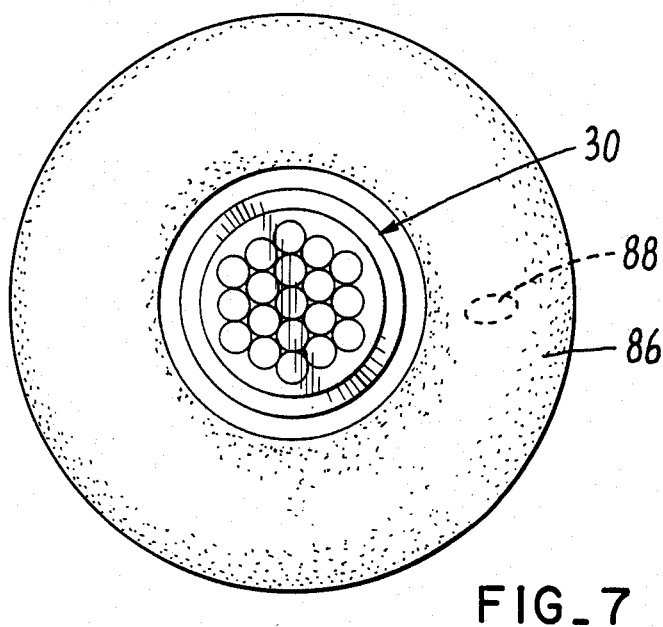
FIG_7

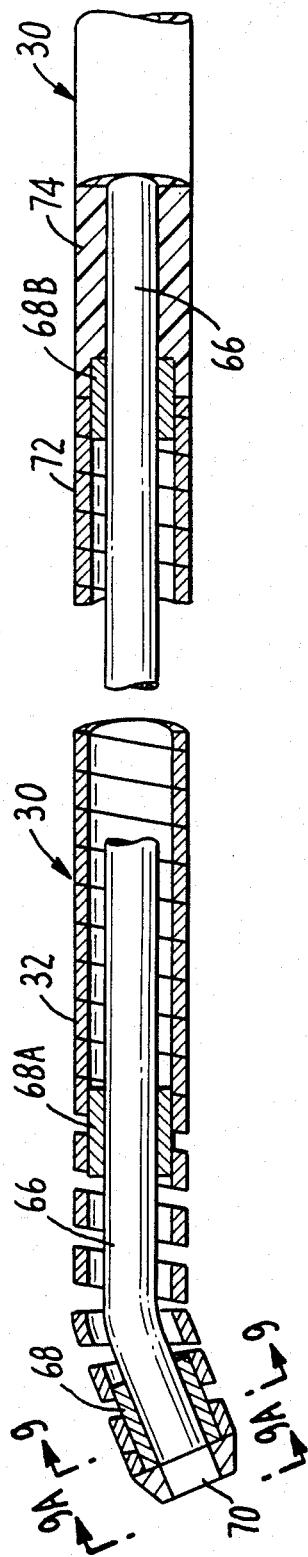
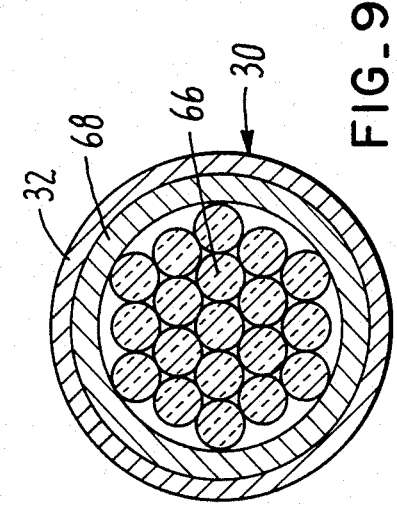
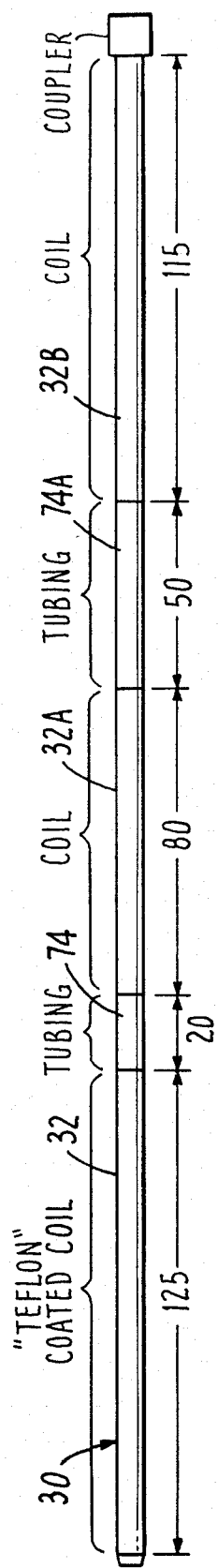
FIG_8  FIG_9  FIG_9A  FIG_10

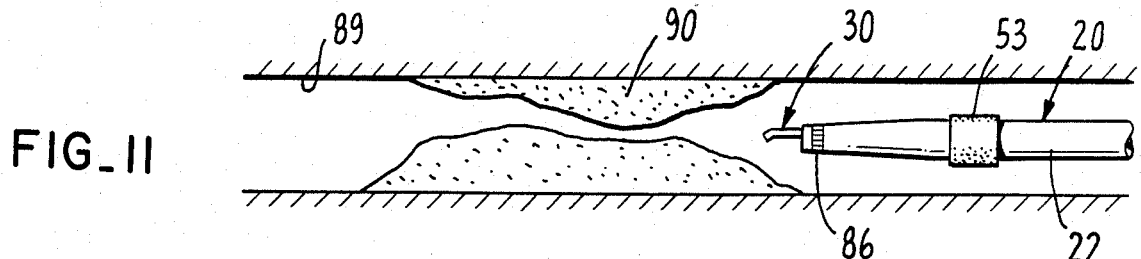
FIG_11
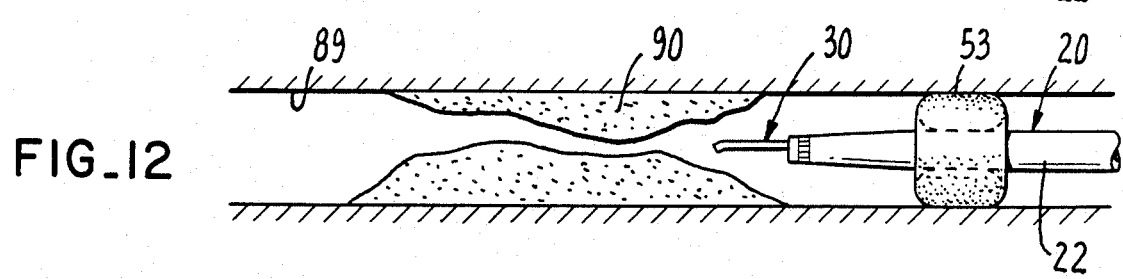
FIG_12
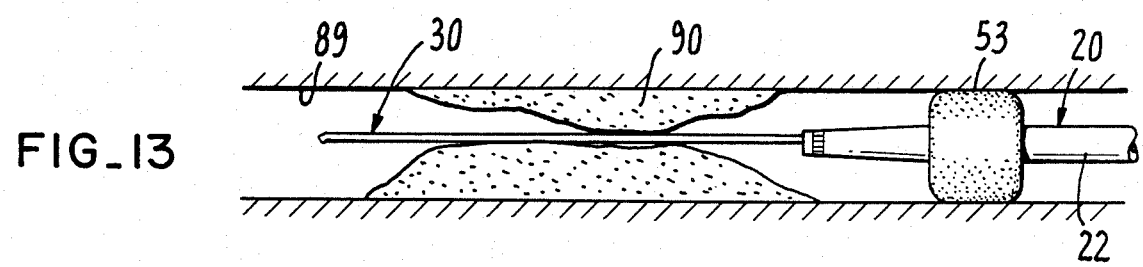
FIG_13
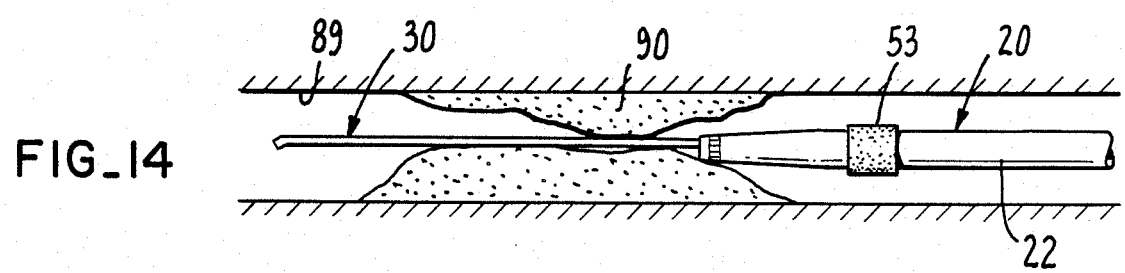
FIG_14
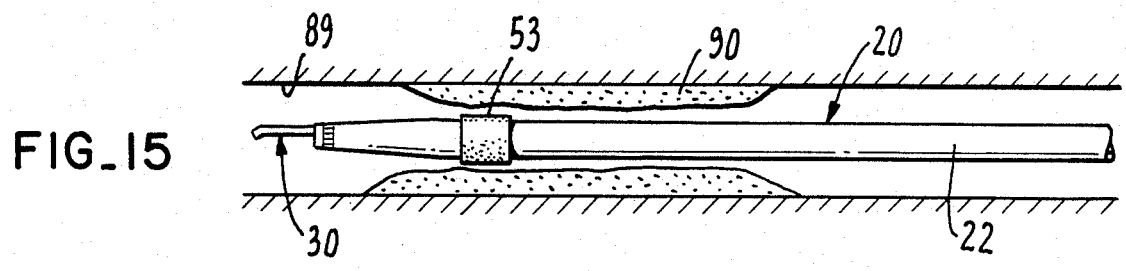
FIG_15
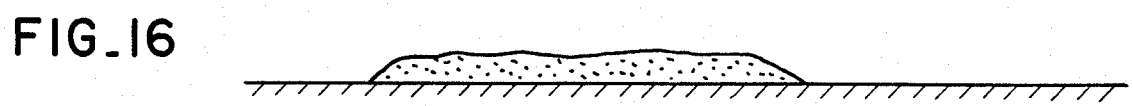
FIG_16

METHOD AND APPARATUS FOR REDUCING BLOCKAGE IN BODY CHANNELS

FIELD OF INVENTION

This invention pertains to the use of lasers in medicine, and more particularly to the guidance and positioning of light radiation using elongated, flexible transfer conduits for diagnostic use and/or therapeutic removal of obstructive disease in an internal body channel or cavity.

BACKGROUND OF THE INVENTION

Disease deposits which cause reduction of flow of body fluids in internal body channels occur in various body sites including the arteries, the ureters and the bile ducts. Conventional surgical techniques which are used to remove the obstructive material include operative procedures and minimally invasive procedures. In an operative procedure, skin incision directly exposes the disease site to facilitate removal of diseases. In a minimally invasive procedure, a surgical instrument is inserted percutaneously (through the skin) into a body channel or cavity and advanced to the disease site. The instrument may use various means (e.g. mechanical, chemical, photophysical) to remove the diseased area and restore normal flow.

In various techniques heretofore conceived for using laser energy as a means to remove diseased areas within body channels, the laser energy enters the proximal end of a radiation transfer conduit (e.g. an optical fiber), travels through the fiber and exits from a more distal operative end within the body channel to reach the treatment site. A major difficulty with these prior techniques was in providing adequate means for non-traumatically guiding the operative end of the radiation transfer conduit to the treatment area and then providing a sufficiently efficient means for removing all or a large portion of the diseased obstruction. Body channels may tortuously curve and branch and the radiation transfer conduit must therefore be flexible and yet maneuverable and controllable. Since manipulation of the transfer conduit must be controlled at one end thereof, the conduit must be capable of responding to both torsional and pushing forces applied to its proximal end. Furthermore, during the obstruction removal process, the radiation transfer conduit must often pass through an area of obstruction to treat more distal areas wherein and beyond a lesion. In some situations, the obstruction may be quite large compared with the size of the beam of laser energy being applied. Therefore, in order to dissolve or reduce such obstructions the beam must be moved or additional treatment means must be utilized to reduce the obstructions after an initial or new channel has been made through the obstruction. Moreover, when any radiation transfer conduit is moved within the body channel, it is essential that its laser energy not be directed at non-contiguous sites within the obstructive deposits, and thereby avoid creating a hazard of embolic events. In addition, the newly created channel must be sufficiently wide to permit adequate re-establishment of the flow of body fluid despite the requirement of using a low profile radiation transfer conduit. Finally, the aforesaid problems were further complicated by specific site factors that often occur at different types of disease areas (e.g. atherosclerosis, uretheral stones, gallstones).

In U.S. Pat. No. 4,641,650 a method is disclosed for destroying atheromatous plaque within an artery of a patient using a catheter system including fiberoptical cable means which includes optical diagnostic means and a treatment fiber optical array means. The diagnostic means is used to sense the presence and location of the plaque in the artery so that the treatment means can be directed on the plaque and avoid damaging healthy tissue. However, despite the improvements in treatment results afforded by the aforesaid sensing system, there existed a need for a more effective system for removing body channel obstructions, and moreover one that was compatible with and could encorporate the sensing system.

Accordingly, a general object of the invention is to provide an improved method of delivering laser energy for the treatment of an area within a body channel or cavity.

Another object of the invention is to teach an improved method and to provide an instrument usable in said method capable of tunneling through a body channel or cavity and of also providing guidance and positioning capabilities that will provide an improved treatment modality in terms of safety and efficacy.

Another object of the invention is to teach an improved method and provide an instrument for enlarging an opening within a body channel or cavity by providing a means to deliver laser energy to contiguous area of diseases and thus diminish the chance of embolic events.

Yet another, more specific object of the invention is to provide an improved instrument of radiation transfer which can be inserted into a body channel having an obstruction and then be controlled to create or enlarge a first opening through the obstructive body channel such that said instrument can advance further through this first channel and thereafter serve as a directional guide for another component of the instrument capable of providing subsequent treatment when operationally interfaced with the diseased site.

Still another object of the present invention is to provide a catheter assembly for removing obstructions from a body channel wherein a first movable guidewire element with radiation capabilities is movable within a second larger catheter body having at least one radiation transfer conduit, so that the first element can be positioned to form an initial opening in the body channel obstruction being treated and then can serve as a guide means to advance the second larger catheter body so that its radiation transfer cnduit can be positioned near the channel obstruction to further dissolve diseased tissue and greatly enlarge the opening through the obstruction.

SUMMARY OF THE INVENTION

In accordance with one aspect of the invention, there is contemplated a method of removing atheromatous plaque to create a new channel within an artery of a patient comprising the steps of introducing a first fiberoptical, light transmitting conduit into the artery and advancing its distal end so that it is operatively opposite the plaque site. At the appropriate time laser energy is introduced into the proximal end of this first fiberoptical conduit which is emitted from its distal end to remove disease deposits and thereby allow the fiberoptical conduit to form a new channel and advance further in the artery. The first conduit is movable within a larger catheter body which also has a second fiberoptical conduit fixed therein. After the first, movable conduit has formed a new channel in an obstruction, the catheter body is guided by and tracks along the first fiberoptical conduit to become operatively interfaced with any remaining atherosclerotic obstruction. With the second fiberoptical conduit so positioned, laser energy is introduced into its proximal end to exit its distal end and remove additional disease deposits contiguous to the new channel, thereby producing a wider channel along the axis of the first fiberoptic conduit. In addition to or in lieu of the use of laser energy through the second conduit the catheter body may also utilize other treatment means at the disease site (e.g. dilatation balloon, slicing device, ultrasonic energy), to widen further the new channel along the axis of the first fiberoptical conduit.

To implement the method of the invention, it is contemplated that the first conduit comprise a single strand or bundle of light transmitting fibers at least the distal end of which is situated within a relatively flexible coated wire sheath capable of serving as a guide means within the body channel being treated. This first conduit means is movable within the catheter assembly having the second fiberoptic conduit. Using linear and torsional control of the first fiber conduit instrument with its coiled wire sheath, the physcan operator can then manipulate and position its distal end within the artery even during the emission of light radiation from the operative end. Thus, the first fiber conduit can first create an enlarged channel and then advance through it. The catheter assembly with its fixed fiber conduit can then track over the first fiber conduit, encounter the disease areas contiguous to the new channel, and operate to widen the channel, either with the application of more laser energy or by performing a conventional dilatation balloon angioplasty.

In accordance with the invention when used to remove atherosclerotic plaque from an artery, the first fiber conduit with its coiled wire exterior serves as a guidewire as it is advanced across an area of constriction in the body channel. Thereafter, the catheter body having single or multiple lumens and single or multiple fiber conduits can be moved forwardly along the first fiber conduit which rests within the lumen of said catheter assembly. After the first conduit has provided partial reduction of the artery plaque, additional laser energy can be directed into the proximal end of the fiber or fibers of the catheter body to remove more diseased tissues when encountered and thus widen the channel in the contiguous area of disease adjacent to the guidewire like fiber conduit.

Other objects, advantages, features of the invention will be apparent from the following detailed description of preferred embodiments thereof, presented in conjunction with the accompanying drawings.

BRIEF DESCRIPTION OF DRAWINGS

FIG. 1 is a partially schematic and fragmentary view in elevation of a catheter assembly embodying principles of the present invention.

FIG. 2 is an enlarged view in section taken at line 2—2 of FIG. 1.

FIG. 3 is an enlarged view in section taken at line 2—2 of FIG. 1 showing a ballon section of the assembly, with the inflated balloon shown in dotted lines.

FIG. 4 is a further enlarged distal end view of the catheter assembly of FIG. 1, taken at line 4—4 thereof.

FIG. 5 is an enlarged distal end view of a modified form of catheter assembly according to the invention.

FIG. 6 is an enlarged distal end view of another modified form of catheter assembly according to the invention.

FIG. 7 is an enlarged distal end view of another modified form of catheter assembly according to the invention.

FIG. 8 is a fragmentary view in elevation and in section showing the movable guidewire/fiber means for the catheter assembly of FIG. 1.

FIG. 9 is a view in section of the guidewire/fiber means taken at line 9—9 of FIG. 8.

FIG. 9A is a distal end view of the guidewire/fiber means taken at line 9A-9A thereof.

FIG. 10 is a schematic view in elevation of the guidewire/fiber means of FIG. 8 showing different sections along its length.

FIGS. 11-16 are a series of schematic views showing one mode of an operation for the removal of atheromatous plaque from an artery in accordance with the principles of the present invention.

DETAILED DESCRIPTION OF EMBODIMENTS

With reference to the drawing, FIG. 1 shows a catheter instrument 20 for removing diseased obstructions from body channels, such as etheromatous plaque from an artery, in accordance with principles of the present invention. In broad terms, the instrument comprises a multi-lumen thin-walled flexible body 22 having a tapered distal end 24 that is adapted for initial insertion into an artery or vein. This flexible body 22 is preferably made from a suitable plastic material such as polyethylene or polyurethane, although other flexible materials could also be used. Near its proximal end 26, the device is coupled, by a suitable conduit coupling 27, to a plurality of branch conduits connected from certain controllable appliances to lumens within the body 22, as will be described below. Within one lumen 28, as shown in FIG. 2, is a movable, first radiation transmission conduit 30 which also serves as a guidewire and has a surrounding coiled wire sheath 32. Separated by a septum 34 from the first lumen 28 in the body 22 is a second lumen 36 within which is a second laser transmission conduit 38 that is fixed in place and is thus non-movable therein.

As shown in FIG. 2, a pair of additional lumens 40 and 42 are provided at spaced apart locations extending along the length of the body 22. Both of these lumens are smaller in diameter than the lumens 28 and 36. One lumen 40 is connected to a flexible tube 44 at the proximal end of the catheter body 22 and has an opening 46 in the wall of the body near its distal end. The tube 44 is adapted for connection to a source of pre-selected liquid such as a suitable radio opaque dye substance that may be used during a treatment procedure with the instrument 20. The proximal end of the lumen 42 is connected to a flexible tube 48 that is connectable to a source of air pressure through a suitable coupling and valve (not shown).

As shown in FIG. 3, an opening 50 from the distal end of the lumen 42 is provided in the wall of the catheter body 22. This opening is located between the ends of an elastomeric tubular sleeve 52 that extends around the body 22 and is retained by suitable annular sealant members 54 at its opposite ends. When compressed air is supplied to the lumen 42, it exits the opening 50 and inflates the sleeve 52 which forms a toroidal balloon around the catheter body, as indicated by the dotted lines in FIG. 3. During use of the instrument 20, this balloon 52 may be used to stabilize the instrument within a body channel and also block the flow of blood during a treatment operation. Attached to the outer surface of the catheter body 22 under the balloon 52 is marker band 63 of a suitable radiation opaque material such as nickel platinum alloy which enables the exact location of the balloon to be monitored during an operation. Similar marker bands may be attached to the catheter body such as near its tapered tip.

At the proximal end 26 of the catheter body 22, the lumen 36 for the fixed laser transmission conduit 38 is connected via a short circuit 55 to a "Y" fitting 56 having a pair of branch members 58 and 60. One branch member 58 contains an extension 62 of conduit 38 that terminates with a coupling which facilitates its connection to a laser generator indicated schematically by the box 64. The other branch member 60 is tubular and has a shutoff valve 65 with an end fitting 67 that facilitates its connection to a selected source of liquid such as a saline solution that may be used in a typical body channel treatment procedure. Lumen 28 for the movable laser transmitting guide wire 30, like conduit 38, terminates with a coupling that facilitates its connection to laser generator 76.

The movable laser transmission conduit 30 that is slidable and rotatable within the lumen 28 will be described in detail with reference to FIGS. 8-10. Throughout its length the conduit 30 has a core 66 of uniform cross-section formed of either a single glass fiber strand or a bundle of glass fibers, as shown, capable of transmitting laser energy. Surrounding the glass fiber core 66 for most of the length of the conduit 30 is the coiled wire sheath 32. This wire is preferably rectangular in cross-section and is made of a resilient, non-corrosive metal such as stainless steel. The sheath 32 is spaced radially outwardly from the core by a series of insulative annular spacers 68 which are preferably made of a radiation opaque material such as a nickel platinum alloy so that, like the markers 63, they serve as internal markers for a physician during a fluoroscopic treatment procedure. As shown in FIG. 8, at the distal end of the movable member 30 is a short tip portion 70 having a modified "J" shape that forms a small angle (e.g. 2°–5°) with the longitudinal axis of the member 30. An annular spacer 68 is provided within this tip portion to secure the front end of the fiber core to the surrounding wire coil 32 and to mark its extreme distal end during use. The distal end of the wire coil on the tip portion 70 is preferably tapered to a smaller diameter.

Spaced longitudinally inwardly from the tip portion 70 is another spacer-marker 68A. As shown in FIG. 8, a front section of the wire coil sheath 32 extends longitudinally to a termination point 72 where it surrounds a third annular spacer 68B and abuts against a shorter section 74 of a plastic material such as polyethylene or polyurethane and having the same outer diameter but completely surrounding the glass fiber core 66. Since this plastic section is essentially bonded or fixed to the fiber core, it provides a means for applying a torsional or twisting force to the entire movable conduit 30.

As shown in FIG. 10, a complete movable conduit 30 preferably has at least two plastic sections 74 and 74A. Thus, in the embodiment shown, the conduit 30 is comprised of the front or first wire coil section 32 having a length of around 125 cms; the second section 74, which is plastic having a length of 20 cms; a third wire coil section 32A having a length of 80 cms; a fourth section 74A which is plastic, having a length of 50 cm; and a fifth section 32B of coiled wire having a length of 115 cm. The latter wire section has a suitable end coupler for the surrounded core which is connectable to a laser generator 76 (FIG. 1). The aforesaid length dimensions are presented as being typical for a particular application of the device 20, but they may vary for different operational procedures.

The two plastic sections 74 and 74A afford alternative locations where torsional force can be applied to turn the conduit 30 about its longitudinal axis and thus change the direction of the laser energy emitted from its distal tip portion 70. The coil wire sheath 32 around the laser transmitting core affords the conduit 30 with a degree of flexibility that enables it to bend when necessary and to be controllable by torsional and pushing forces at its proximal end. Yet it also has a sufficient degree of stiffness that enables the conduit to function as a guide wire for the main catheter body 22, to help move it through a body channel after the conduit 30 has initially moved beyond the distal end of the body 22. Thus, as the conduit 30 emits laser energy from its distal end to destroy diseased tissue, it may be moved longitudinally (as well as be rotated) within the catheter body 22 until it extends a substantial distance beyond the end of the catheter body. Now, as the catheter body is also moved forwardly in the body channel to further remove blocking plaque or tissue, the member 30 is sufficiently strong to serve as a guide means for the catheter body.

In the embodiment of the invention shown in FIGS. 2 and 4, the lumens 28 and 36 containing the first movable radiation transmission element 30 and the fixed radiation transmission conduit 38 are both cylindrical and their centerlines spaced apart from the centerline of the catheter body 22. Also, the lumen 36 for the fixed glass fiber conduit 38 has a slightly smaller diameter than the lumen 28 for the movable element 30. With this embodiment, the entire catheter body 22 would be rotated in use so that the fixed laser transmission conduit 38 can move in an arc to direct laser energy against blocking tissue in the body channel being treated.

In a modified arrangement for a instrument 20A, shown in FIG 5, the centerline of the lumen 28 for the movable radiation conduit 30 is coincident with the centerline of the catheter body 22. Circumferentially spaced around the lumen 28 are a series of three arcuately shaped lumens 78 in the catheter body 22. Each of these arcuate lumens contains a plurality of glass fibers 80, each thereby forming a separate laser transmission conduit. With these circumferentially spaced apart arcuate shaped conduits, rotational movement of the catheter body 22 can be minimized and laser energy can be supplied through any of the selected fiberoptic conduits 80 in use, as will be explained more fully below.

A further modified form of the invention is shown in FIG. 6 which is a front end view of an instrument catheter assembly 20B. Here, the lumen 28 for the movable radiation conduit 30 has a centerline that is spaced from the main catheter centerline. Spaced to one side of the lumen 28 is a second lumen 82 having a generally arcuate or "V-like" shape within which are fixed a plurality of glass fibers 84 for transmitting laser energy. This latter lumen, which is fully packed with glass fibers, covers a large percentage of the frontal cross-sectional area of the catheter body 22 so that the laser energy emitted therefrom can be directed toward a substantial area of obstructive material within a body channel with little or no rotational movement of the catheter body during treatment.

In another embodiment of the invention, a catheter assembly 20C is shon in FIG. 7 with the lumen 28 for the movable radiation conduit 30 being centrally located within the catheter body 22 so that its centerline is coincident with the body centerline. Here, near the end of the distal end of the catheter body, an inflatable balloon 86 is provided in lieu of a lumen having fixed fiber optic strands for transmitting laser energy. An opening 88 to the inside oof this balloon is provided at the distal end of another lumen provided within the catheter body 22 for supplying compressed air to inflate the balloon 86.

A typical operation of the instrument 20 in accordance with principles of the present invention will be described with reference to FIGS. 11–16 utilizing the example of the removal of an atheromatous plaque from an artery 89 as shown in FIG. 11. Before treatment commences, the distal end of the movable radiation conduit 30 is inserted into the lumen 28 of the catheter body 22, and the proximal end of this movable element is connected to the laser generator system, as shown in FIG. 1. The distal end of the catheter body 22 is inserted into the patient's artery and is moved to near the treatment site, i.e., the arterial blockage 90. A guiding catheter (not shown) of the type well know in the art, may be used to initially place the instrument 20 within the patient's artery or body channel. As shown in FIG. 12, the toroidal balloon 52 on the catheter body 22 can be inflated to block the artery and stabilize the body 22. The distal end of the movable radiation conduit 30 is then advanced beyond the distal end of catheter body 22 until it is operatively opposite the treatment site 90. The glass fiber core within the conduit 30 can now transmit and receive light radiation from the treatment site. At this point, the conduit 30 can be used to sense the direction and proximity of diseased blocking tissue in accordance with the principles of U.S. Pat. No. 4,641,650. At the appropriate time, the laser generator 76 is activated to transmit laser energy into the proximal end of the fiber conduit 30 which is emitted from its distal end, thereby illuminating a portion of the treatment site 90. The impinged portion of atherosclerosis is vaporized and the movable conduit 30 is advanced into the resultant crater which ultimately becomes a larger opening through the diseased tissue. This process is repeated until the distal end of the movable conduit has advanced completely through the lesion as shown in FIG. 13. This advancement may require torsional as well as linear manipulation of the movable conduit 30 applied by the physician on its proximal end (which remains external to the body 22) in order to negotiate curves in the artery.

In a related embodiment of the invention, the movable fiber optic conduit 30 is inserted into the lumen 28 of the catheter body 22 and in a similr fashion the entire catheter assembly 20 is inserted into an artery to be treated. The movable fiber conduit 30 is moved to the blockage lesion where it utilizes laser energy with its guidance and positioning functions to create a new channel in the treatment site. Once the movable fiber element is distal to the lesion or treatment site, the catheter body 22 is advanced along its axis until the distal end of the fixed optical fiber conduit 38 in the catheter body is operatively opposite the remaining atherosclerotic areas, as shown in FIG. 14. With the fixed glass fiber conduit 38 so positioned, the second laser generator means 64 is activated to transmit light radiation or laser energy into the proximal end of the fixed optical fiber conduit 62. Energy from this fixed conduit 38 illuminates the portion of the atherosclerotic lesion contiguous to the movable fiber conduit 30, more plaque is removed and the new channel is widened. During activation of the fixed fiber conduit, the entire catheter body 22 may be rotated to some degree to sweep an additional cross sectional area of the blockage lesion. The process of tissue removal by laser energy may continue until the lesion is reduced in size and a clinically successful result is achieved, as shown in FIGS. 15 and 16. At this point, with the channel through the blocking lesion 90 substantially increased, the entire catheter instrument 20 can be advanced, and the movable conduit 30 can be pushed further into the artery 89 ahead of the body 22.

Once the conduit 30 is distal to the lesion 90, the catheter body 22 may be advanced further along the axis of the movable conduit 30 which at this point serves as a guide wire for the catheter body. When the catheter body 22 reaches the lesion area, dilatation balloon 53 similar to the balloon 52 or the frontal balloon 86 of FIG. 7 may be positioned across the remaining atherosclerotic plaque area as shown in FIG. 15. A conventional balloon angioplasty can be then performed if desired to further widen the body chanel at this point.

Using the embodiment of FIG. 4, the catheter body 22 may be rotated at least partially as the fixed fiber conduit 38 is transmitting laser energy, so that a greater area of lesion being treated can be swept and thus removed. With the embodiment of FIG. 5 this can be accomplished by selective activation of the fixed plural fiber conduits 80. If the embodiment of FIG. 6 is utilized, an increased cross sectional area of blockage tissue can be contacted and vaporized with little or no rotational movement of the catheter body 22 when laser energy is transmitted through the "V-shaped" fiber conduit 84. With both embodiments, the movable conduit 30 is utilized to accomplish the initial enlargement of the body channel being treated and thereafter, the fixed conduits 80 or 84 are energized (with some partial rotation of the catheter body 22, when necessary) to remove additional diseased tissue or plaque and further enlarge the channel.

While only the treatment of plaque has been described herein, the present invention may be used for the treatment of other diseases which include but are not limited to blood clots, foreign bodies in non-vascular channels, tumors, stones in the urinary tract and gall bladder as well as prostate obtstructions. The movable radiation transfer conduit 30 can be but is not limited to a fiberoptic conduit which can be a single fiber or multiple fibers. The fiberoptic cable can be coupled with other catheter designs which include, but are not limited to, such features as endoscopy, balloon devices, steerable guiding systems, multiple lumens for infusion and suctioning, ultrasonic guidance, monitoring devices, ablation devices such as mechanical rotors, slicers or ultrasonic pulverizers, magnetic resonance imaging means, pressure, flow or temperature monitoring and catheter devices. The operative end of the radiation transfer conduits can include but are not limited to be at the distal tip of the fiber coils or catheters, can be directed at angles, focus or expand the laser beam, protected by transparent windows circumferential or through balloon materials located other than at the distal tip.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. An instrument for removing an obstruction in an internal body channel comprising:
   an elongated catheter body adapted for insertion into a body channel having a first lumen throughout its length, said catheter body having a proximal end and an opposing distal end;
   an elongated movable guide and laser transmission conduit means extending through said lumen of said catheter body and having a distal end that is extendable beyond the distal end of said catheter body and a proximal end, said proximal end of said conduit means adapted to be connected to a controlled source of laser energy; and
   treatment means at the distal end of said catheter body for further reducing said obstruction following preliminary penetration thereof by said elongated movable guide and laser transmission means, wherein said treatment means comprises a laser transmission means fixed within a lumen of said catheter body and terminating at its distal end.

2. The instrument as described in claim 1 including an inflatable means affixed to the outer surface of said catheter body near its distal end for sealingly engaging the interior walls of the body channel.

3. The instrument as described in claim 1 wherein said treatment means comprises a plurality of glass fibers in a closely packed conduit having generally a circular cross-section, whose centerline is offset from the centerline of said catheter body.

4. The instrument as described in claim 1 wherein said treatment means comprises a plurality of glass fibers in a closely packed conduit having generally a crescent shape that partially surrounds said elongated movable guide and laser transmission conduit means.

5. The instrument as described in claim 1 wherein said treatment means comprises a plurality of fixed laser transmission conduit means spaced radially from and circumferentially spaced around said lumen of said catheter body.

6. The instrument as described in claim 5 wherein said plurality of fixed laser transmission conduit means comprises three spaced apart groups of closely packed glass fibers, all terminating at the distal end of said catheter body, each said group being connectable to a laser power source.

7. The instrument as described in claim 1 wherein said treatment means in said catheter body further comprises an inflatable means at its distal end which can be utilized to perform an angioplasty function on a diseased area of body channel following initial penetration thereofy by said elongated movable guide and laser transmission conduit means.

8. The instrument as described in claim 1 wherein elongated movable guide and laser transmission conduit means comprises an elongated member comprised of an outer coil of wire surrounding an inner core of fibero;ptic material.

9. The instrument as described in claim 1 wherein said catheter body is made of a flexible plastic material having a plurality of lumens along its length.

10. The instrument as described in claim 1 wherein said catheter body is less flexible than said elongated movable guide and laser transmission conduit means.

11. The instrument as described in claim 1 wherein said elongated movable guide and laser transmission conduit means is substantially longer than said catheter body and is comprised of at least one major section of length having an outer sheath formed from a wire coil surrounding a core of fiberoptic material, said coil being formed from wire having a rectangular cross section with coils being arranged close together, whereby said conduit means provides a guidewire function for advancing said catheter body in the body channel after it has utilized laser energy to remove the obstruction therein.

12. A method for removing an obstruction in an internal body channel, the method comprising the steps of:
   inserting an elongated catheter body into the body channel being treated, said catheter body having a proximal end and an opposing distal end;
   moving a combined guidewire and laser transmission conduit through said catheter body so that it extends beyond its distal end and near the channel obstruction being treated;
   transmitting laser energy through said combined guidewire and laser transmission conduit and emitting it so as to destroy at least a portion of the channel obstruction and thereby provide an increased opening through the obstruction as the conduit moves forwardly therein;
   further reducing said obstruction by emitting laser energy from a treatment means positioned at the distal end of said catheter body; and
   thereafter utilizing said combined guidewire and laser transmission conduit to guide said catheter body further along into said body channel.

13. The method as set forth in claim 12 including the further steps of:
   moving said catheter body along said combined guidewire and laser transmission conduit to a position close to said increased opening in said obstruction; and
   using said treatment means to further reduce the size of the obstruction and thereby increase the cross-sectional area of the opening through the obstruction.

14. The method as set forth in claim 13 further including dilating an expandable balloon near the distal end of said catheter body to further reduce said obstruction.

15. The method as set forth in claim 13 further including slowly rotating said catheter body as laser energy is transmitted through its distal end, thereby sweeping an arcuate cross-sectional area of the obstruction in said body channel.

16. The method as set forth in claim 13 further including transmitting laser energy in bursts through a selected one or more of a plurality of laser transmission conduits in said catheter body whose ends are circumferentially spaced apart at its distal end.

17. A method for removing an obstruction in a body channel, the method comprising the steps of:
   providing a flexible guidewire device having a fiber optic core, a proximal end portion, and distal end portion that can be advanced, retracted or rotated by axial or torsional manipulation and control of the device at a location near its proximal end portion;

inserting said guidewire device within a lumen of a larger catheter body having a proximal end and a distal end corresponding to the proximal end portion and the distal end portion of the guidewire device;

positioning said catheter body within a body channel;

moving said guidewire device through said catheter body to the proximity of a body channel obstruction;

transmitting laser energy through the core of said guidewire device to enlarge an opening through said obstruction and advancing said guidewire device within said opening;

utilizing said guidewire device to guide said catheter body as it moves further along in the body channel closer to the obstruction opening;

moving said catheter body along said guidewire device to a position close to said obstruction opening; and using treatment means at the distal end of the catheter body to further reduce the size of the obstruction and thereby increase the cross-sectional area of the opening through the obstruction, wherein said treatment means comprises a laser transmission means and said further reduction of said obstruction is effected by emission of laser energy from said laser transmssion means.

18. The method as set forth in claim 17 further including dilating an expandable balloon near the distal end of said catheter body to further reduce said obstruction.

19. The method as set forth in claim 17 further including slowly rotating said catheter body as laser energy is transmitted through its distal end, thereby sweeping an arcuate cross-sectional area of the obstruction in said body channel.

20. The method as set forth in claim 17 further including transmitting laser energy in bursts through a selected one or more of a plurality of laser transmission conduits in said catheter body whose ends are circumferentially spaced apart at its distal end.

21. An instrument for removing an obstruction in an internal body channel comprising:

(a) an elongated catheter body having a proximal end and a distal end, the distal end of which is adapted for insertion into a body channel, and having a first lumen including a proximal end and a distal end corresponding to the proximal and distal ends of said catheter body;

(b) a movable, elongated, combination guiding and laser transmission device positioned within said first lumen and adapted for transmitting laser energy to an arteriosclerotic site in a blood vessel, the combination guiding and laser transmission device including a flexible sheathing surrounding said transmission device for at least a substantial portion of its length said sheating having a proximal end and a distal end corresponding to the proximal and distal ends of said catheter body, and having sufficient stiffness so that said device can be pushed through a body channel and turned therein by force applied near its proximal end and can also serve as a tracking means for said catheter body; and (c) treatment means at the distal end of said catheter body for reducing the obstruction, wherein said treatment means comprises a fixed laser transmission means contained within a second lumen of said catheter body.

22. The device as described in claim 21 wherein said sheating is a coiled metal wire.

23. The device as described in claim 22 wherein said coiled wire has a rectangular cross section and the coils are close together.

24. The device as described in claim 22 wherein said metal sheathing has a modified "J" shaped tip at its distal end for ease of reaching arteriosclerotic sites within a blood vessel.

25. The device as described in claim 21, wherein said combination guiding and laser transmission device comprises a bundle of glass fibers.

26. The device as described in claim 21, wherein at least one opaque marker is provided at said distal end of said elongated catheter body, so that accurate positioning of the catheter body within a body channel can be controlled under fluoroscopy when in use.

27. The device as described in claim 26, wherein a plurality of opaque markers are provided at spaced intervals between said distal and proximal ends of said elongated catheter body.

28. The device as described in claim 26, wherein at least one intermediate portion of said combination guiding and laser transmission device is covered with an annular section of plastic material which enables a torsional force to be applied for turning the transmission device within said catheter body and within a body channel being treated.

* * * * *